(12) United States Patent
Schiff et al.

(10) Patent No.: US 11,633,537 B1
(45) Date of Patent: Apr. 25, 2023

(54) DRUG DELIVERY ASSEMBLY INCLUDING A PRE-FILLED CARTRIDGE

(71) Applicant: Fresenius Kabi Deutschland GmbH, Bad Homburg (DE)

(72) Inventors: David R Schiff, Highland Park, NJ (US); Jason Zerweck, Media, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/180,594

(22) Filed: Feb. 19, 2021

(51) Int. Cl.
| | |
|---|---|
| *A61M 5/142* | (2006.01) |
| *A61M 5/20* | (2006.01) |
| *A61M 5/168* | (2006.01) |
| *A61K 47/60* | (2017.01) |
| *A61K 38/19* | (2006.01) |

(52) U.S. Cl.
CPC ........ *A61M 5/14248* (2013.01); *A61K 38/193* (2013.01); *A61K 47/60* (2017.08); *A61M 5/16881* (2013.01); *A61M 5/2033* (2013.01); *A61M 2205/50* (2013.01); *A61M 2205/8206* (2013.01)

(58) Field of Classification Search
CPC .......... A61M 5/14248; A61M 5/16881; A61M 5/2033; A61M 2205/50; A61M 2205/8206; A61M 2039/0229; A61M 2005/2492; A61M 5/1413; A61M 5/1456; A61M 5/14566; A61M 2005/14573; A61M 2005/14268; A61M 2005/2403; A61M 2005/2407; A61M 2005/2411; A61M 2005/2414

USPC .......................................................... 604/135
See application file for complete search history.

(56) References Cited

U.S. PATENT DOCUMENTS

| | | | |
|---|---|---|---|
| 7,981,102 B2 * | 7/2011 | Patel | A61M 5/1413 |
| | | | 128/DIG. 1 |
| 2002/0169439 A1 * | 11/2002 | Flaherty | A61P 9/10 |
| | | | 604/891.1 |
| 2003/0167036 A1 | 9/2003 | Flaherty | |
| 2008/0091139 A1 * | 4/2008 | Srinivasan | A61M 5/30 |
| | | | 604/68 |

(Continued)

FOREIGN PATENT DOCUMENTS

| | | | |
|---|---|---|---|
| WO | 2018081234 A1 | 5/2018 | |
| WO | 2018183039 A1 | 10/2018 | |

(Continued)

*Primary Examiner* — Bhisma Mehta
*Assistant Examiner* — Nidah Hussain
(74) *Attorney, Agent, or Firm* — Cook Alex Ltd.

(57) ABSTRACT

A drug delivery assembly includes a main body and a cartridge. The body includes a housing, an adhesive pad, and a body interface that detachably associates with a cartridge interface of the cartridge. A fluid flow path extends through the body housing, between a first end configured to open a seal of the cartridge and a second end configured to enter a human body. The cartridge contains a drug reservoir having an outlet and holding a medicament. The seal prevents the medicament from exiting the reservoir and maintains pressure within the reservoir until the seal is opened by the first end of the fluid flow path when the cartridge is coupled to the main body, placing the reservoir into fluid communication with the flow path. A controller actuates a valve within the body to selectively allow and prevent flow through the flow path during an automated drug delivery routine.

30 Claims, 3 Drawing Sheets

(56) References Cited

U.S. PATENT DOCUMENTS

| | | | |
|---|---|---|---|
| 2009/0131860 A1* | 5/2009 | Nielsen | A61M 5/14248 604/66 |
| 2011/0178461 A1* | 7/2011 | Chong | A61B 17/3415 604/151 |
| 2012/0010594 A1 | 1/2012 | Holt et al. | |
| 2015/0306307 A1* | 10/2015 | Cole | A61M 5/158 604/508 |
| 2015/0374919 A1 | 12/2015 | Gibson | |
| 2016/0038689 A1 | 2/2016 | Lee et al. | |
| 2016/0199574 A1 | 7/2016 | Ring et al. | |
| 2016/0220798 A1* | 8/2016 | Netzel | A61M 5/145 |
| 2016/0296704 A1 | 10/2016 | Gibson | |
| 2016/0354555 A1 | 12/2016 | Gibson et al. | |
| 2017/0119969 A1 | 5/2017 | McCullough et al. | |
| 2017/0124284 A1 | 5/2017 | McCullough et al. | |
| 2017/0147787 A1 | 5/2017 | Albrecht et al. | |
| 2017/0182253 A1 | 6/2017 | Folk et al. | |
| 2017/0340837 A1 | 11/2017 | Nazzaro et al. | |
| 2017/0361015 A1 | 12/2017 | McCullough | |
| 2017/0368260 A1 | 12/2017 | McCullough et al. | |
| 2018/0021508 A1 | 1/2018 | Destefano et al. | |
| 2018/0028747 A1 | 2/2018 | Hanson et al. | |
| 2018/0036476 A1 | 2/2018 | McCullough et al. | |
| 2018/0085517 A1 | 3/2018 | Laurence et al. | |
| 2018/0256823 A1 | 9/2018 | Nazzaro et al. | |
| 2018/0272059 A1 | 9/2018 | Marbet et al. | |
| 2018/0304014 A1 | 10/2018 | Knudsen et al. | |
| 2019/0022306 A1 | 1/2019 | Gibson et al. | |
| 2019/0050375 A1 | 2/2019 | Fitzgibbon et al. | |
| 2019/0060562 A1 | 2/2019 | Olivas et al. | |
| 2019/0083702 A1 | 3/2019 | Nekouzadeh et al. | |
| 2019/0134296 A1 | 5/2019 | Barbedette et al. | |
| 2019/0143043 A1 | 5/2019 | Coles et al. | |
| 2019/0143047 A1 | 5/2019 | Jazayeri et al. | |
| 2019/0151544 A1 | 5/2019 | Stonecipher | |
| 2019/0167908 A1 | 6/2019 | Fitzgibbon et al. | |
| 2019/0192766 A1 | 6/2019 | Stonecipher | |
| 2019/0247579 A1 | 8/2019 | Damestani | |
| 2019/0275241 A1 | 9/2019 | Ring et al. | |
| 2019/0321544 A1* | 10/2019 | List | A61M 5/14248 |
| 2019/0328965 A1 | 10/2019 | Moberg | |
| 2019/0365986 A1 | 12/2019 | Coiner et al. | |
| 2019/0374707 A1 | 12/2019 | Damestani et al. | |
| 2019/0381238 A1 | 12/2019 | Stonecipher et al. | |
| 2020/0023122 A1 | 1/2020 | McCullough et al. | |
| 2020/0086044 A1* | 3/2020 | Streit | A61M 5/14248 |
| 2020/0164145 A1 | 5/2020 | Chang et al. | |
| 2020/0164155 A1 | 5/2020 | Mojarrad et al. | |
| 2020/0179609 A1 | 6/2020 | Tan-Malecki et al. | |
| 2020/0197628 A1 | 6/2020 | McCullough et al. | |
| 2020/0206429 A1 | 7/2020 | Hering et al. | |
| 2020/0230313 A1 | 7/2020 | Mojarrad et al. | |
| 2020/0238004 A1* | 7/2020 | McCullough | A61M 5/14248 |
| 2020/0254172 A1 | 8/2020 | Forster et al. | |
| 2020/0261648 A1 | 8/2020 | Groszmann et al. | |
| 2020/0261657 A1 | 8/2020 | Gibson et al. | |
| 2020/0289745 A1 | 9/2020 | Harris et al. | |
| 2020/0297927 A1 | 9/2020 | Conrath et al. | |
| 2020/0322793 A1 | 10/2020 | Yang | |
| 2020/0338271 A1 | 10/2020 | Harris et al. | |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

DRUG DELIVERY ASSEMBLY INCLUDING A PRE-FILLED CARTRIDGE

BACKGROUND

Field of the Disclosure

The present disclosure relates to drug delivery devices. More particularly, the present disclosure relates to devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

Figure 1:
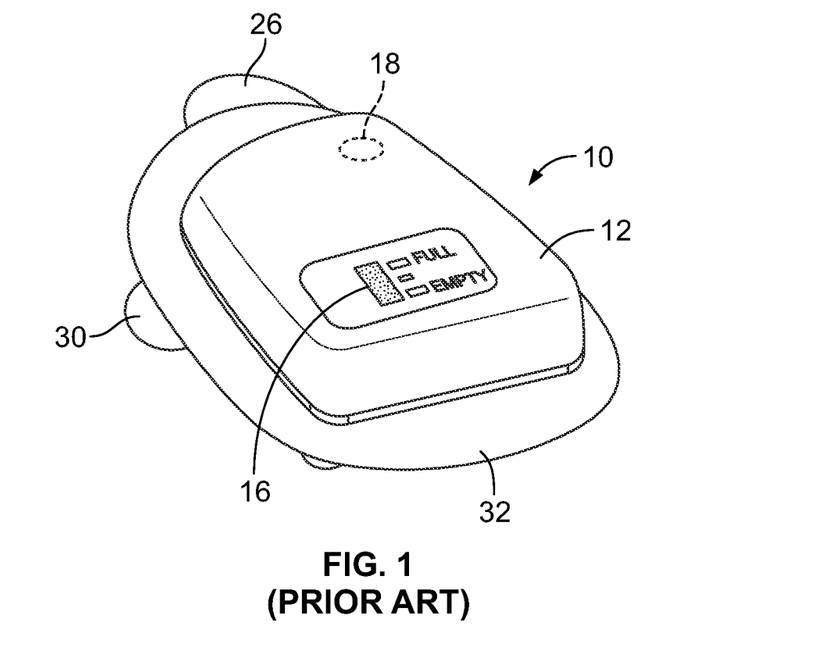
FIG. 1 is a top perspective view of a drug delivery device according to conventional design.
Figure 2:
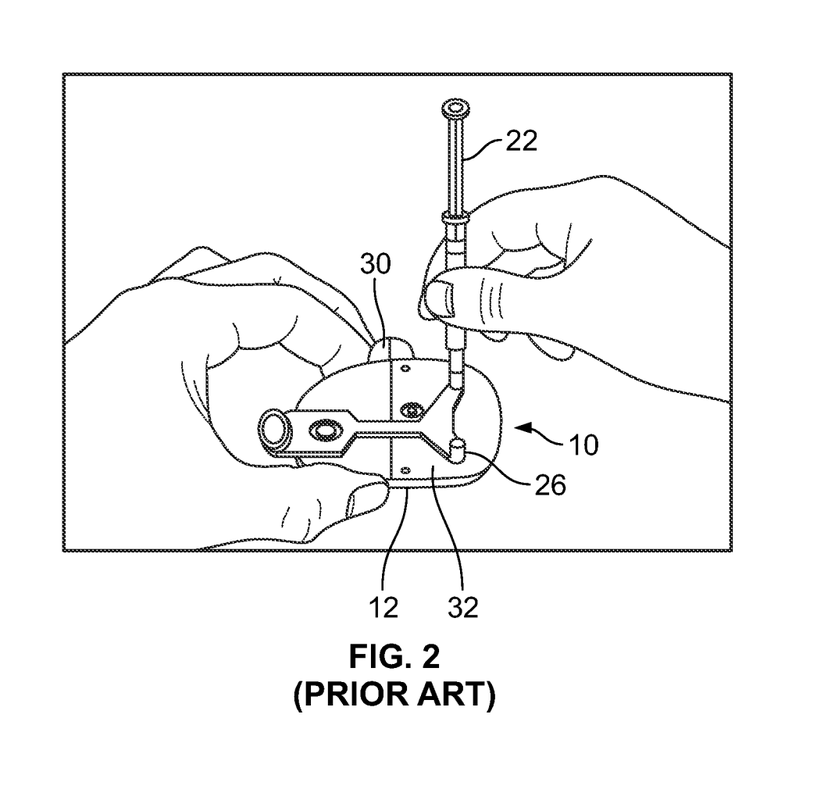
FIG. 2 is a bottom perspective view of the drug delivery device of FIG. 1.
Figure 3:
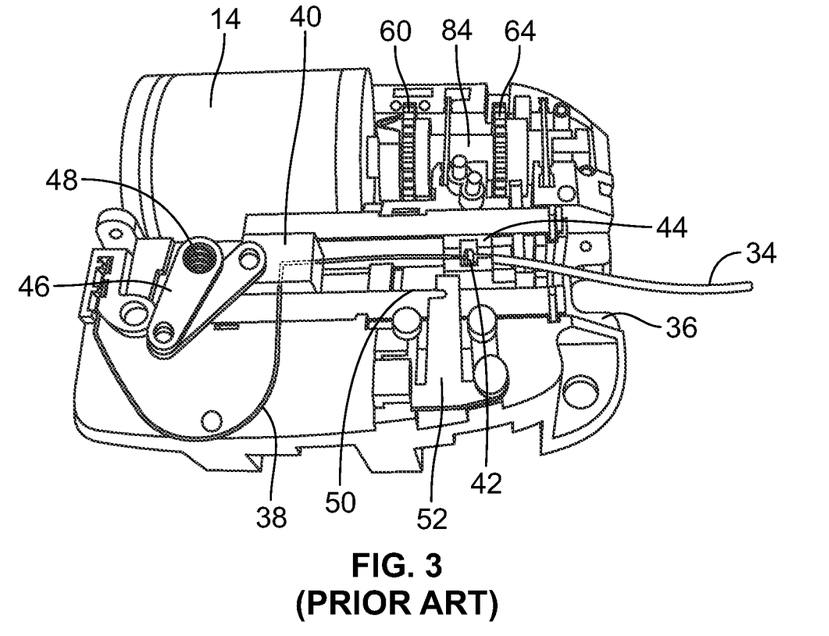
FIG. 3 is a top perspective view of the interior components of the drug delivery device of FIG. 1.
Figure 4:
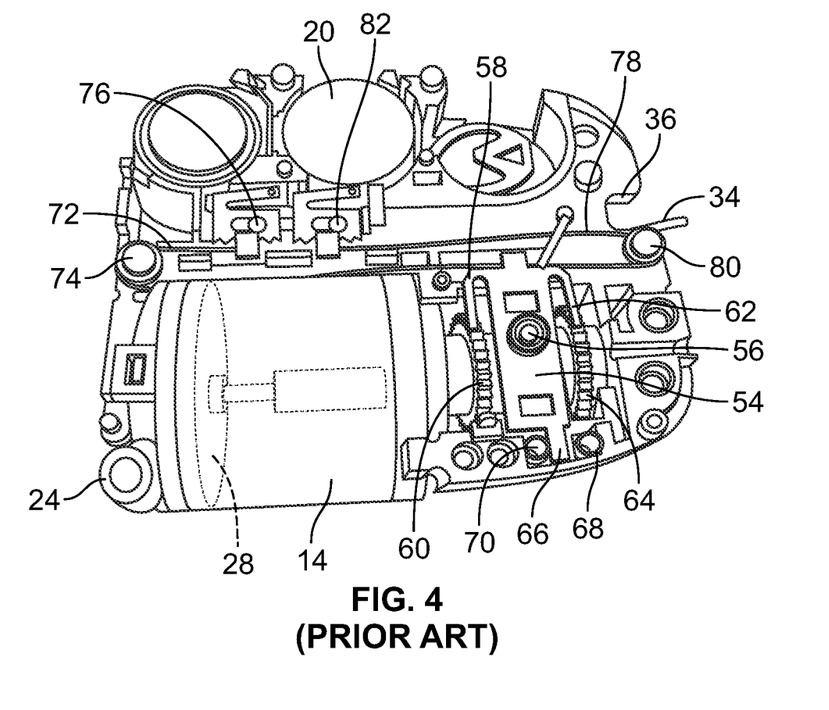
FIG. 4 is a bottom perspective view of the interior components of the drug delivery device of FIG. 1.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, such devices integrate the drug reservoir into the housing of the device, which makes the device a single-use article that must be disposed of after use. Thus, it would be advantageous to provide a device configured to allow refill and reuse, rather than requiring removal and replacement of the entire device after every use.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug delivery assembly is disclosed. The assembly includes a main body including a body housing having upper and lower surfaces and a body interface. The body housing includes a body latch and defines a docking area. A fluid flow path extends through the body housing between a first end and a second end. The second end is configured to enter a human body. A valve is associated with the fluid flow path. The valve is configured to alternately allow and prevent fluid flow between the first and second ends of the fluid flow path. The main body also includes a controller. The controller is configured to actuate the valve to selectively allow and prevent fluid flow through the fluid flow path during a drug delivery routine. The main body also has an adhesive pad associated with the lower surface of the housing. The adhesive pad is configured to removably attach to a human body surface.

The assembly also includes a cartridge. The cartridge has a cartridge housing. The cartridge housing is sized and configured to be at least partially received by the docking area of the main body. The cartridge housing includes a cartridge interface configured to be associated to the body interface when the cartridge housing is at least partially received by the docking area. The cartridge housing also includes a cartridge latch configured to detachably or permanently associate with the body latch when the cartridge interface is associated to the body interface. A drug reservoir is positioned within the cartridge housing. The drug reservoir includes an outlet and contains a medicament. A piston is movably associated with the drug reservoir, and a spring is associated with the piston. The spring is configured to bias the piston toward the outlet of the drug reservoir. Finally, the cartridge includes a seal. The seal prevents flow of the medicament out of the drug reservoir via the outlet. When the cartridge housing is at least partially received by the docking area, the first end of the fluid flow path is configured to engage and open the seal so as to place the fluid flow path into fluid communication with the outlet of the drug reservoir.

In another aspect, a main body is provided for use in combination with a drug delivery cartridge of the type including a cartridge housing having a cartridge interface, a cartridge latch, and a drug reservoir positioned within the cartridge housing. The main body includes a body housing having upper and lower surfaces and a body interface. The body housing includes a body latch and defines a docking area configured to receive at least a portion of the cartridge, so as to associate the body interface to the cartridge interface and to detachably or permanently associate the body latch with the cartridge latch. A fluid flow path extends through the body housing between a first end and a second end. The first end is configured to engage and open a seal of the cartridge when the cartridge housing is at least partially received by the docking area, so as to place the fluid flow path into fluid communication with an outlet of the drug reservoir. The second end of the fluid flow path is configured to enter a human body. A valve is associated with the fluid flow path and is configured to alternately allow and prevent fluid flow between the first and second ends of the fluid flow path. The main body also includes a controller. The controller is configured to actuate the valve to selectively allow and prevent fluid flow through the fluid flow path during a drug delivery routine. The main body also has an adhesive pad associated with the lower surface of the housing. The adhesive pad is configured to removably attach to a human body surface.

In yet another aspect, a drug delivery cartridge is provided for use in combination with a main body of the type including a body housing having upper and lower surfaces and a body interface and defining a docking area. The drug delivery cartridge includes a cartridge housing sized and configured to be at least partially received by the docking area of the main body. The cartridge housing includes a cartridge interface configured to be associated to the body interface when the cartridge housing is at least partially received by the docking area. The cartridge also includes a cartridge latch configured to detachably or permanently associate with a body latch when the cartridge interface is associated to the body interface. A drug reservoir is positioned within the cartridge housing. The drug reservoir includes an outlet and contains a medicament. A piston is movably associated with the drug reservoir. A spring is associated with the piston and is configured to bias the piston toward the outlet of the drug reservoir. The cartridge also includes a seal preventing flow of the medicament out of the drug reservoir via the outlet. The seal is configured to be engaged and opened by a first end of a fluid flow path of the main body when the cartridge housing is at least partially received by the docking area, so as to place the outlet of the drug reservoir into fluid communication with the fluid flow path.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 5:
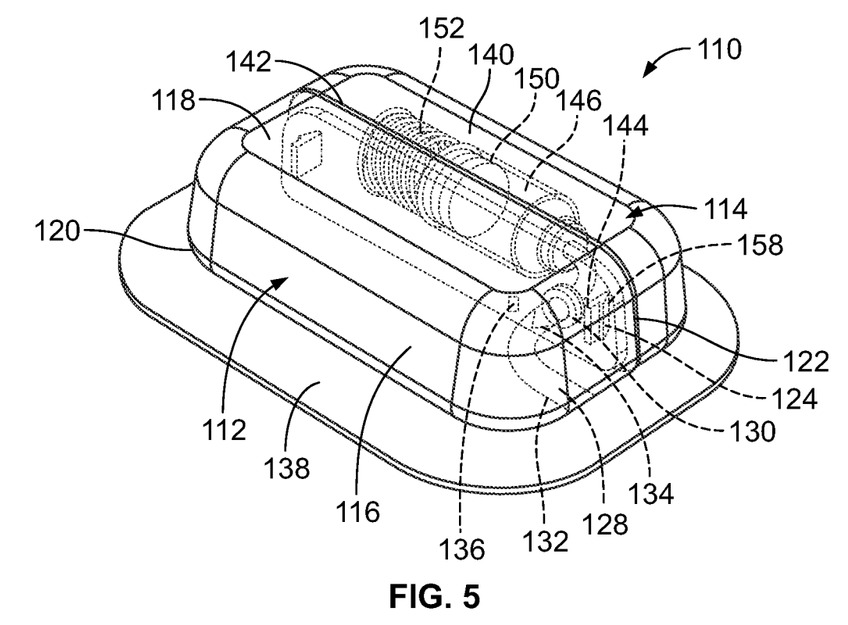
FIG. 5 is a top perspective view of an exemplary embodiment of a drug delivery assembly according to an aspect of the present disclosure.
Figure 6:
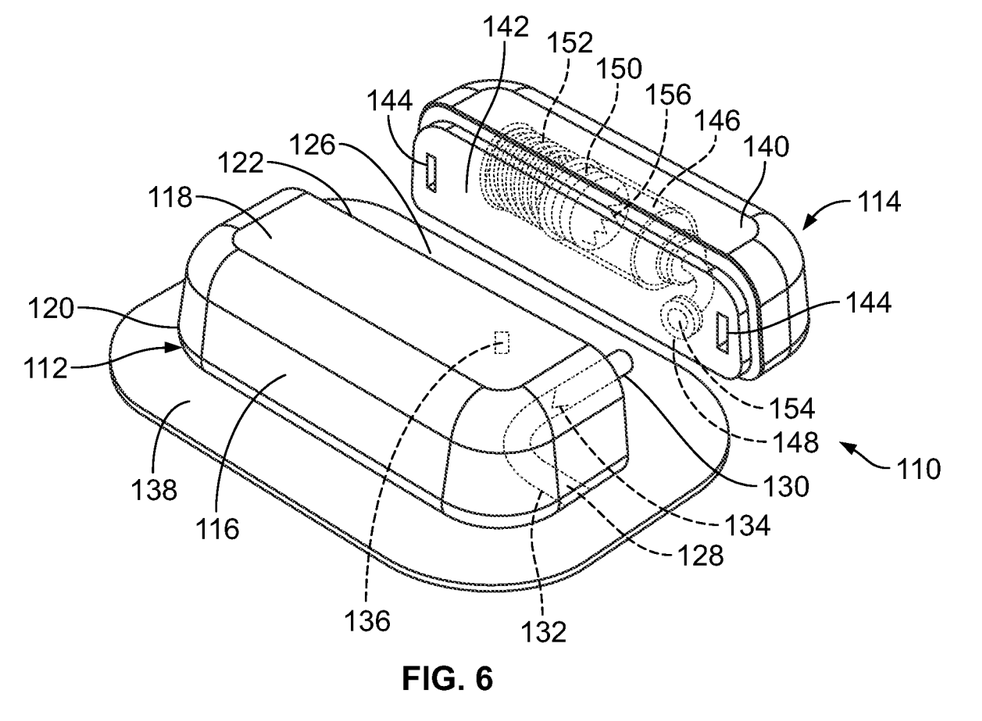
FIG. 6 is a top perspective view of the assembly of FIG. 5, showing a cartridge of the assembly separated from a main body of the assembly.

FIGS. 5 and 6 show an exemplary embodiment of a drug delivery assembly 110 according to the present disclosure. The drug delivery assembly 110 includes a main body 112 and a cartridge 114. FIG. 5 shows the main body 112 coupled to the cartridge 114, while FIG. 6 shows the main body 112 separated from the cartridge 114.

The main body 112 includes a body housing 116 having upper and lower surfaces 118 and 120 and a body interface 122. The body housing 116 may be made from any suitable, generally rigid material, including plastic polymers such as polyvinyl chloride (PVC), polypropylene, polycarbonate, and polystyrene. The body interface 122 may be defined by a side wall of the body housing 116 extending from the upper surface 118 to the lower surface 120. The body housing 116 includes a body latch 124 and defines a docking area 126 positioned adjacent to the body interface 122 (shown in FIG. 6). The body latch 124 may be associated with the body interface 122, facing the docking area 126, or may instead be incorporated into the docking area 126. It is also within the scope of the present disclosure for a plurality of body latches 124 to be provided, which may include embodiments in which two or more body latches 124 are incorporated into only the body interface 122, embodiments in which two or more body latches 124 are incorporated into only the docking area 126, and embodiments in which at least one body latch 124 is incorporated into each of the body interface 122 and the docking area 126. If a plurality of body latches 124 is provided, they may be similarly or differently configured.

A fluid flow path 128 extends through the body housing 116 between a first end 130 and a second end 132. The fluid flow path 128 may be variously configured without departing from the scope of the present disclosure, including having one or more portions that are defined by an interior surface of the body housing 116, one or more portions that are defined by an exterior surface of the body housing 116, and/or one or more portions that are defined by components associated with or incorporated into the body housing 116. The first end 130 of the fluid flow path 128 may be associated with the body interface 122, while the second end 132 may be associated with or positioned adjacent to the lower surface 120 of the body housing 116 and configured to enter a human body. In an exemplary embodiment, the second end 132 of the fluid flow path 128 is configured as a needle and/or a cannula (e.g., of the type described above with regard to the device 10 of FIGS. 1-4) configured to penetrate a human body surface, such that the fluid flow path 128 may form a fluid connection between the first end 130 and a human body to which the drug delivery assembly 110 is secured.

A valve 134 is associated with the fluid flow path 128. The valve 134 is configured to alternately allow and prevent fluid flow between the first 130 and second 132 ends of the fluid flow path 128. Any suitable valve may be used, with the particular configuration of the valve 134 depending upon the configuration of the portion of the fluid flow path 128 with which it is incorporated, which may include the valve 134 being configured as a pinch valve or a ball valve, for example.

The main body 112 also includes a controller 136 coupled to a power source (e.g., a battery). The controller 136 is configured to command the various electrical components of the drug delivery assembly 110 to execute a drug delivery routine, which may include any of a number of possible steps, including actuating the valve 134 (either directly or via an intermediary electronic device) to selectively allow and prevent fluid flow through the fluid flow path 128. The controller 136 may be variously configured without departing from the scope of the present disclosure, with the controller 136 being provided in an exemplary embodiment as a CPU or MPU configured as a computer chip mounted to a printed circuit board positioned within the body housing 116 that carries programmable software for executing the drug delivery routine.

The valve 134 may be a mechanically actuated valve. For example, in an embodiment, the controller 136 may be coupled to a mechanical member, such that the mechanical member moves when commanded by the controller 136. In such an embodiment, the mechanical member is mechanically associated with the valve 134, such that when the mechanical member moves the valve 134 also moves. The mechanical member may be a lever or linkage which moves from a first position or condition to a second position or condition, when commanded by the controller 136. When the mechanical member is in the first position, the valve 134 is configured to move to, or remain in, a first position with the valve 134 closed, preventing fluid flow from the first end 130 of the flow path 128 to the second end 130 of the flow path 128. When the mechanical member is moved to the second position, the valve 134 moves from the first position to a second, open position, allowing fluid to flow from the first end 130 of the flow path 128, through or around the valve 134 and to the second end 132 of the flow path 128. The controller 136 may be programmed to control the mechanical member to alternately move the valve 134 between its first and second positions to selectively allow and prevent fluid flow between first and second ends 130 and 132 of the fluid flow path 128 during a drug delivery routine, as will be explained in greater detail.

Alternatively, the valve 134 may be an electrically actuated valve, such that the controller 136 is coupled to the valve 134 by an electrical connection, with the controller 136 controlling a component of the valve 134 (e.g., a solenoid) to move between two conditions or positions. When commanded by the controller 136, or when electricity is not flowing to the valve 134, the valve 134 (or at least a component thereof) will be in a first position or condition in which fluid flow is prevented through the fluid flow path 128. When commanded by the controller 136, the valve 134 (or at least a component thereof) will be in a second position or condition in which fluid flow between the first and second ends 130 and 132 of the fluid flow path 128 is prevented. Accordingly, the controller 136 may be configured to, alternately and selectively, allow and prevent fluid flow between the first and second ends 130 and 132 of the fluid flow path 128 during a drug delivery routine, as will be described in greater detail.

The main body 112 also has an adhesive pad 138 associated with the lower surface 120 of the housing 116. The adhesive pad 138 is configured to removably attach to the human body surface. Any suitable medical grade adhesive pad configured to be removably attached to the human body surface may be used, such as one of the type described above with regard to the device 10 of FIGS. 1-4.

As for the cartridge 114, it includes a cartridge housing 140 (formed of any suitable, generally rigid material, such as a PVC or other plastic material) that is sized and configured to be at least partially received by the docking area 126 of the main body 112. The cartridge housing 140 includes a cartridge interface 142 configured to be associated to the body interface 122 when the cartridge housing 140 is at least partially received by the docking area 126. In the embodiment shown, the cartridge interface 142 protrudes from the cartridge housing 140. The body interface 122 is recessed from the docking area 126, so as to mate with the cartridge interface 142 upon association, while the docking area 126 may protrude, so as to receive at least a portion of the cartridge housing 140. Though this configuration is shown, in alternative embodiments other configurations may be used for associating the cartridge interface 142 with the body interface 122 and the cartridge housing 140 with the docking area 126.

The cartridge housing 140 also includes a cartridge latch 144 (illustrated in FIG. 6 as a pair of latches 144) configured to detachably or permanently associate with the body latch 124 when the cartridge interface 142 is associated to the body interface 122. On account of the cartridge latch 144 being configured to mate or otherwise be complementary to the body latch 124, the configuration, position, and orientation of the cartridge latch 144 will depend upon the configuration, position, and orientation of the body latch 124. In the illustrated, exemplary embodiment, the body latch 124 is associated with the body interface 122, with the cartridge latch 144 being associated with a corresponding region of the cartridge interface 142. In such an embodiment, when a user advances the cartridge 114 toward the main body 112, the cartridge interface 142 and body interface 122 are brought into contact with each other, with the cartridge housing 140 at least partially received by the docking area 126 and the cartridge latch 144 engaged by the body latch 124 to prevent the cartridge 114 from being dissociated from the main body 112. When a drug delivery routine is completed, the user separates the main body 112 and the cartridge 114, such as by disengaging the body and cartridge latches 124 and 144 and moving the cartridge 114 away from the main body 112. In an exemplary embodiment, one or both of the latches 124 and 142 are spring-loaded, in which case the user may disengage the latches 124 and 142 by pressing or otherwise manipulating a portion of the latch or latches 124 and 142 to actuate the spring and release the latches 124 and 142.

The cartridge 114 and main body 112 are to remain in association during a drug delivery routine, so it may be advantageous to provide the assembly 110 with a lock 158 (FIG. 5) configured to associate with the body latch 124 and/or the cartridge latch 142. If provided, the controller 136 may be configured to actuate the lock 158 to prevent disengagement of the body latch 124 and the cartridge latch 144 during the drug delivery routine. The controller 136 may also be configured to actuate the lock 158 to allow disengagement of the body latch 124 and the cartridge latch 144 after the end of the drug delivery routine. For example, the controller 136 may be configured to be activated upon the cartridge 114 being associated to the main body 112 (i.e., when the latches 124 and 144 are engaged). Upon being activated, the controller 136 may actuate the lock 158 to prevent dissociation of the latches 124 and 144. Alternatively, the lock 158 may be configured to automatically actuate upon association of the latches 124 and 144, without intervention from the controller 136. At the end of a drug delivery routine, the controller 136 commands the lock 158 (which may include preventing the flow of electricity to the lock 158 or a component of the lock 158) to deactivate or disengage, thereby allowing the latches 124 and 144 and, hence, the cartridge 114 and the main body 112 to be separated.

A drug reservoir 146 is positioned within the cartridge housing 140. The drug reservoir 146 includes an outlet 148 (shown in FIG. 6) and contains a medicament 156 (shown in FIG. 6). In all embodiments described herein, the medicament may be any suitable fluid medication. In an exemplary embodiment, the medicament may be pegfilgrastim, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin. In any event, the outlet 148 is configured to fluidically connect to the first end 130 of the fluid flow path 128 when the cartridge interface 142 is associated with the body interface 122. The drug reservoir 146 may be made from any suitable, generally rigid material, including but not limited to polyethylene terephthalate (PET), for example.

A piston 150 is movably associated with the drug reservoir 146, and a spring 152 (e.g., a coil spring) is associated with the piston 150. The spring 152 is configured to bias the piston 150 toward the outlet 148 of the drug reservoir 146. A seal 154 is associated with the outlet 148 (e.g., associated with the cartridge interface 142), preventing the medicament 156 from exiting the drug reservoir 146 via the outlet 148, such that biasing the piston 150 toward the sealed outlet 148 will generate pressure within the reservoir 146. The first end 130 of the fluid flow path 128 is configured such that, when the cartridge housing 140 is at least partially received by the docking area 126, the first end 130 of the fluid flow path 128 will engage or contact and open the seal 154 so as to place the fluid flow path 128 into fluid communication with the outlet 148 of the drug reservoir 146. To that end, the first end 130 of the fluid flow path 128 may be configured as a projection (e.g., a generally cylindrical or tubular formation) extending from the housing interface 122 that is at least partially received by the outlet 148 to pierce the seal 154. The seal 154 may be a frangible seal (as shown by the tear markings of the seal 154 in FIG. 6), formed of a thin film or foil material, or may alternatively be configured to be resealable (e.g., as a pre-slit rubber septum).

Thus, when the cartridge 114 is coupled to the body 112, the seal 154 is opened, and the reservoir outlet 148 is placed into fluid communication with the first end 130 of the fluid flow path 128. After the seal 154 is broken, the medicament 156 is allowed to flow from the drug reservoir 146, through the outlet 148, and into the fluid flow path 128 via the first end 130 of the fluid flow path 128. However, on account of the valve 134 being in the first (closed) position, the medicament 156 will not continue flowing to the second end 132 of the fluid flow path 128, such that connecting the cartridge 114 to the main body 112 will not immediately cause a drug to be delivered to a patient. Instead, during the course of a drug delivery routine, the controller 136 will command the valve 134 to selectively move between the first position and the second (open) position in which the medicament 156 may flow to the second end 132 of the fluid flow path 128 to reach the patient. As described above, the drug reservoir 146 is pressurized by operation of the piston 150 and spring 152, such that moving the valve 134 to its open position will depressurize the reservoir 146, allowing the spring 152 to drive the piston 150 and, thus, the medicament 156 toward the outlet 148. The medicament 156 flows out of the drug reservoir outlet 146 via the outlet 148, through the first end 132 of the flow path 128, through the open valve 134, through the second end 132 of the flow path 118 and into the body of the patient.

The controller 136 may be configured to open and close the valve 134 such that a preprogrammed dose of the medicament 156 may be administered each time the valve 134 is opened. This may include the controller being programmed to deliver a plurality of doses on a pre-determined schedule at pre-determined intervals. Alternatively, the controller may be programmed to deliver a single dose of the medicament at a given time.

After completion of the drug delivery procedure, a user may detach the cartridge 114 from the body main 112 and dispose of the cartridge 114. A new pre-filled cartridge 114 may be inserted into the main body 112 when the user needs a subsequent dose of the medicament 156. This configuration allows for refill and reuse of the assembly 110 without removing the main body 112 from the user for subsequent doses of the medicament 156. This configuration also facilitates separate storage of the medicament 156. Accordingly, when a medicament 156 may need to be refrigerated or frozen, the main body 112 may still remain at room temperature and, if necessary, remain adhered to the body of the patient.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug delivery assembly comprising:
 a main body including
  a body housing having an upper surface, a lower surface, and a body interface, the body housing including a body latch and defining a docking area,
  a fluid flow path extending through the body housing between a first end and a second end, the second end configured to enter a human body,
  a valve associated with the fluid flow path and configured to alternately allow and prevent fluid flow between the first and second ends of the fluid flow path,
  a controller, and
  an adhesive pad associated with the lower surface of the housing, the adhesive pad configured to removably attach to a human body surface; and
 a cartridge including
  a cartridge housing sized and configured to be at least partially received by the docking area, the cartridge housing including
   a cartridge interface configured to be associated to the body interface when the cartridge housing is at least partially received by the docking area, and
   a cartridge latch configured to detachably or permanently associate with the body latch when the cartridge interface is associated to the body interface,
  a drug reservoir positioned within the cartridge housing, the drug reservoir including an outlet and containing a medicament,
  a piston movably associated with the drug reservoir,
  a spring associated with the piston and configured to bias the piston toward the outlet of the drug reservoir, and
  a seal preventing flow of the medicament out of the drug reservoir via the outlet, wherein
 the first end of the fluid flow path is configured to engage and open the seal when the cartridge housing is at least partially received by the docking area so as to place the fluid flow path into fluid communication with the outlet of the drug reservoir, and
 the controller is configured to actuate the valve to selectively allow and prevent fluid flow through the fluid flow path during a drug delivery routine.

2. The drug delivery assembly of claim 1, wherein the first end of the fluid flow path is associated with the body interface and the seal is associated with the cartridge interface.

3. The drug delivery assembly of claim 1, wherein the controller is configured to actuate a lock to prevent disengagement of the body latch and the cartridge latch during said drug delivery routine.

4. The drug delivery assembly of claim 3, wherein the controller is configured to actuate the lock to allow disengagement of the body latch and the cartridge latch after the end of said drug delivery routine.

5. The drug delivery assembly of claim 1, wherein at least one of the body latch and the cartridge latch is a spring-loaded latch.

6. The drug delivery assembly of claim 1, wherein the body interface is defined by a side wall of the body housing extending from the upper surface to the lower surface.

7. The drug delivery assembly of claim 1, wherein the body latch is associated with the body interface.

8. The drug delivery assembly of claim 1, wherein the cartridge latch is associated with the cartridge interface.

9. The drug delivery assembly of claim 1, wherein the valve is a mechanically actuated valve.

10. The drug delivery assembly of claim 1, wherein the valve is an electrically actuated valve.

11. The drug delivery assembly of claim 1, wherein the seal is a frangible seal.

12. The drug delivery assembly of claim 1, wherein the medicament comprises pegfilgrastim.

13. The drug delivery assembly of claim 1, wherein the main body includes a conduit defining at least a portion of the fluid flow path.

14. A main body for use in combination with a drug delivery cartridge including a cartridge housing having a cartridge interface, a cartridge latch, a drug reservoir including an outlet and containing a medicament positioned within the cartridge housing, a piston movably associated with the drug reservoir, a spring associated with the piston and configured to bias the piston toward the outlet of the drug reservoir, and a seal preventing flow of the medicament out of the drug reservoir via the outlet, the main body comprising:
 a body housing having an upper surface, a lower surface, and a body interface, the body housing including a body latch and defining a docking area configured to receive at least a portion of the cartridge so as to associate the body interface to the cartridge interface and to detachably or permanently associate the body latch with the cartridge latch;
 a fluid flow path extending through the body housing between a first end and a second end, the second end configured to enter a human body;
 a valve associated with the fluid flow path and configured to alternately allow and prevent fluid flow between the first and second ends of the fluid flow path;
 a controller; and
 an adhesive pad associated with the lower surface of the housing, the adhesive pad configured to removably attach to a human body surface, wherein
 the first end of the fluid flow path is configured to engage and open the seal when the cartridge housing is at least partially received by the docking area so as to place the fluid flow path into fluid communication with the outlet of the drug reservoir, and
 the controller is configured to actuate the valve to selectively allow and prevent fluid flow through the fluid flow path during a drug delivery routine.

15. The main body of claim 14, wherein the first end of the fluid flow path is associated with the body interface.

16. The main body of claim 14, wherein the controller is configured to actuate a lock to prevent disengagement of the body latch and the cartridge latch during said drug delivery routine.

17. The main body of claim 16, wherein the controller is configured to actuate the lock to allow disengagement of the body latch and the cartridge latch after the end of said drug delivery routine.

18. The main body of claim 14, wherein the body latch is a spring-loaded latch.

19. The main body of claim 14, wherein the body interface is defined by a side wall of the body housing extending from the upper surface to the lower surface.

20. The main body of claim 14, wherein the body latch is associated with the body interface.

21. The main body of claim 14, wherein the valve is a mechanically actuated valve.

22. The main body of claim 14, wherein the valve is an electrically actuated valve.

23. The main body of claim 14, wherein the medicament comprises pegfilgrastim.

24. A drug delivery cartridge for use in combination with a main body including a body housing having an upper surface, a lower surface, and a body interface, the body housing including a body latch and defining a docking area, a fluid flow path extending through the body housing between a first end and a second end configured to enter a human body, a valve associated with the fluid flow path, and an adhesive pad associated with the lower surface of the body housing and configured to removably attach to a human body surface, the cartridge comprising:
   a cartridge housing sized and configured to be at least partially received by the docking area, the cartridge housing including
      a cartridge interface configured to be associated to the body interface when the cartridge housing is at least partially received by the docking area, and
      a cartridge latch configured to detachably or permanently associate with the body latch when the cartridge interface is associated to the body interface;
   a drug reservoir positioned within the cartridge housing, the drug reservoir including an outlet and containing a medicament;
   a piston movably associated with the drug reservoir;
   a spring associated with the piston and configured to bias the piston toward the outlet of the drug reservoir; and
   a seal preventing flow of the medicament out of the drug reservoir via the outlet, wherein
      the seal is configured to be engaged and opened by the first end of the fluid flow path when the cartridge housing is at least partially received by the docking area so as to place the outlet of the drug reservoir into fluid communication with the fluid flow path, and
      the drug delivery cartridge omits a controller.

25. The drug delivery cartridge of claim 24, wherein the seal is associated with the cartridge interface.

26. The drug delivery cartridge of claim 24, wherein the cartridge latch is a spring loaded latch.

27. The drug delivery cartridge of claim 24, wherein the cartridge latch is associated with the cartridge interface.

28. The drug delivery cartridge of claim 24, wherein the seal is a frangible seal.

29. The drug delivery cartridge of claim 24, wherein the seal is a resealable seal.

30. The drug delivery cartridge of claim 24, wherein the medicament comprises pegfilgrastim.

* * * * *